(12) United States Patent
Reaume

(10) Patent No.: US 8,777,914 B2
(45) Date of Patent: Jul. 15, 2014

(54) ABSORBENT MEMBER

(76) Inventor: Kimberly Reaume, Fowlerville, MI (US)

( * ) Notice: Subject to any disclaimer, the term of this patent is extended or adjusted under 35 U.S.C. 154(b) by 444 days.

(21) Appl. No.: 13/135,084

(22) Filed: Jun. 25, 2011

(65) Prior Publication Data

US 2012/0330261 A1 Dec. 27, 2012

(51) Int. Cl.
 *A61F 13/15* (2006.01)
(52) U.S. Cl.
 USPC ............. 604/385.03; 604/385.04; 604/385.21
(58) Field of Classification Search
 USPC ............. 604/385.01, 385.03, 385.04, 385.21; D24/124–126
 See application file for complete search history.

(56) References Cited

U.S. PATENT DOCUMENTS

| | | | | |
|---|---|---|---|---|
| 5,439,458 | A * | 8/1995 | Noel et al. | 604/378 |
| 6,908,456 | B1 * | 6/2005 | Drevik | 604/385.04 |
| 7,125,401 | B2 * | 10/2006 | Yoshimasa | 604/392 |
| 7,875,013 | B2 * | 1/2011 | Rubio | 604/385.17 |
| 8,157,779 | B2 * | 4/2012 | Williams | 604/385.101 |
| 2002/0143315 | A1 * | 10/2002 | Garrad et al. | 604/385.04 |

* cited by examiner

*Primary Examiner* — Lynne Anderson
(74) *Attorney, Agent, or Firm* — John G. Chupa

(57) ABSTRACT

An absorbent member 10 having dissimilarly shaped ends 14, 16 which integrally terminate into a middle portion 18 and which cooperatively allow for the selective absorption of menstrual cycle discharge material.

7 Claims, 1 Drawing Sheet

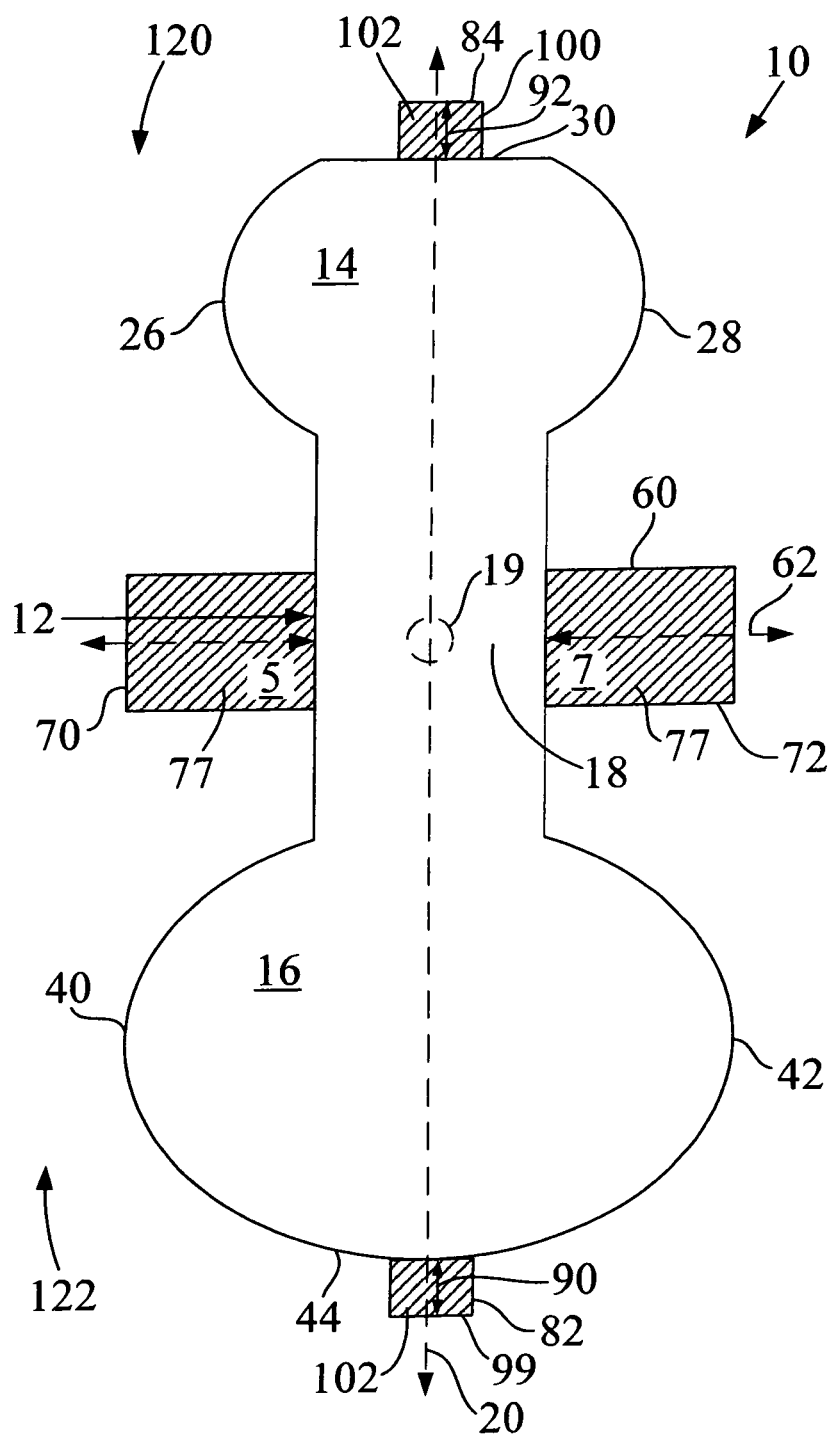

ABSORBENT MEMBER

GENERAL BACKGROUND

1. Field of the Invention

The present invention generally relates to an absorbent member and more particularly to an absorbent member which may be selectively worn by a female and which is adapted to absorb the discharge associated with the menstrual cycle.

2. Background of the Invention

Females undergo a menstrual cycle during which blood and other material discharges from the body. To absorb these menstrual discharges, a variety of absorbing members have been used. For example, one type of member requires physical placement within the body and such a member has been frequently cited as a cause of discomfort and a cause of toxic shock, as well as having other undesirable side effects. Other types of members which do not require physical placement within the body are used but do not securely stay in a desired location and do not fully absorb the discharging material.

There is therefore a need for a new and improved absorbing member which overcomes some or all of the drawbacks associated with current and prior absorbing members and the present invention provides such a member.

SUMMARY OF THE INVENTION

It is a first non-limiting object of the present invention to provide a new and improved absorbing member which overcomes some or all of the previously delineated drawbacks associated with current and prior absorbing members.

It is a second non-limiting object of the present invention to provide a new and improved member to absorb menstrual cycle discharges and which remains in a desired location and which does not require placement within the body.

According to a first non-limiting aspect of the present invention, an absorbent member is provided and includes a pair of dissimilar and generally rounded ends which each terminate into a generally rectangular middle portion; and a plurality of adhesive strips which are respectively coupled to a first of the pair of generally rounded ends, to a second of the pair of generally rounded ends, and to the middle portion.

According to a second non-limiting aspect of the present invention, an absorbent member is provided and includes a body with a first end, wherein the first end has first and second opposed side edges having respective rates of curvature which are constant and equal, wherein the first end further includes a remote edge and wherein each of the two opposed side edges terminate into the remote edge which has a rate of curvature which is less than the respective rates of curvature of the first and second opposed side edges, wherein the body further includes a second end having a second remote edge which has no curvature and third and fourth opposed side edges which have respective rates of curvature which are constant and equal and wherein each of the third and fourth opposed side edges terminate into the second remote edge and wherein the respective rates of curvature of the third and fourth opposed side edges are substantially less than the respective rates of curvature of the first and second opposed side edges and wherein the body further includes a narrow middle portion having a constant width, a first longitudinal axis of symmetry, and which terminates into the first and second end; and wherein the absorbent member further includes a generally rectangular adhesive strip which has a second longitudinal axis of symmetry which is orthogonal to the first longitudinal axis of symmetry, which is pliable, and which has a center portion which is coupled to the middle portion and which has two and substantially identical adhesive bearing ends which project away from the middle portion; and wherein the absorbent member further includes second and third adhesive strips which each include a respective first end which is respectively coupled to the first and second ends of the body and which each include a respective second adhesive bearing end which respectively project away from the first and second ends of the body and wherein each of the adhesive strips have a respective third and fourth longitudinal axis of symmetry and wherein each of the third and fourth longitudinal axes of symmetry overlay the first longitudinal axis of symmetry.

These and other features, aspects, and advantages will become apparent from a reading of the following detailed description of the preferred embodiment of the invention, including the subjoined claims, and by reference to the following drawings.

BRIEF DESCRIPTION OF THE DRAWINGS

FIG. 1 is a top view of an absorbent member which is made in accordance with the teachings of the preferred embodiment of the invention.

DETAILED DESCRIPTION OF THE PREFERRED EMBODIMENT OF THE INVENTION

Referring now to FIG. 1, there is shown an absorbent member 10 which is made in accordance with the teachings of the preferred embodiment of the invention.

Particularly, member 10 has a generally flat body 12 with a pair of dissimilarly shaped ends 14, 16. End 14 is generally goblet shaped, in one non-limiting embodiment of the invention, and end 16 is generally elliptically shaped in a non-limiting embodiment of the invention. Each end 14, 16 integrally terminates into a generally rectangular shaped middle portion 18 and body 12 has a longitudinal axis of symmetry 20.

Moreover, end 14 has a pair of side edges 26, 28 and the edges 26, 28 integrally terminate into an outer edge 30. Together, the edges 26, 28, and 30 cooperatively define the general goblet shape of the end 14. In one non-limiting embodiment of the invention, the rate of curvature of each of the edges 26, 28 is equal and the edge 30 has no appreciable curvature and defines a straight line segment. In one non-limiting embodiment the rate of curvature of each edge 26, 28 has a rate of curvature of one degree per inch, although other degrees of curvature may be utilized.

The end 16 has a pair of side edges 40, 42 and an outer edge 44 which integrally terminates into each of the side edges 40, 42. In one non-limiting embodiment, the rates of curvature of each edge 40, 42 are equal and these rates of curvature, of the edges 40, 42, are appreciably larger than the rates of curvature of the edges 26, 28. In one non-limiting embodiment the rates of curvature of edges 40, 42 is about three degrees per inch, although other rates of curvature may be utilized. Together the edges 40, 42, 44 cooperatively define an elliptical shape.

Further, the absorbent member 10 includes a first adhesive strip or portion 60 which may be generally rectangular in shape and which has a longitudinal axis of symmetry 62. The portion 60 is attached to the portion 18, by the use glue or a pin (shown in phantom by reference numeral 19), such that the longitudinal axis of symmetry 62 is orthogonal to the longitudinal axis of symmetry 20. Moreover, in this configuration, ends 70, 72 of the portion 60 project in opposed opposite directions from the portion 18 and respectively contain adhesive 77 (i.e., in one non-limiting embodiment respective outer surfaces 5, 7 contain adhesive 77).

Member 10 further includes a pair of substantially identical adhesive members 82, 84 (each of which is dissimilar from adhesive member 60). Each member 82, 84 had a respective longitudinal axis of symmetry 90, 92 and each member 82, 84 is attached to body 12 such that the respective longitudinal axes of symmetry 90, 92 of each member 82, 84 respectively overlays the longitudinal axis of symmetry 20. Such attachment may be made by glue or a pin or other type of fastener. Moreover, each respective end surfaces 99, 100 of portions 82, 84 contain adhesive 102.

In operation, the body 12 (which is pliable and may be constructed of cotton) is selectively folded. End 14 is moved in direction 120 and end 16 is moved in direction 122. In this manner, the end 16 overlays the anal opening of a user while the end 14 overlays the vaginal opening of the user, thereby blocking and absorbing menstrual cycle discharge. The adhesive 77 (on the portion 60) and the adhesive 102 (on the portions 99, 100) are made to be in contact with the body of the person or some undergarment, thereby cooperatively ensuring that the member 10 remains in a desired location. After the member 10 has fully absorbed the discharge or the cycle is over, the member 10 may be discarded by forcing the adhesive 77, 102 to be out of contact with whatever such adhesive 77, 102 was respectively in contact with and then dislodging the member 10 from whatever position such member 10 occupied. In this manner, the member 10 may be selectively discarded.

It is to be understood that the present inventions are not limited to the exact construction which has been illustrated, but that various changes and modifications may be made without departing from the spirit and the scope of the inventions as they are further delineated in the following claims.

What is claimed is:

1. An absorbent member having a body with a first end, wherein said first end has first and second opposed side edges having respective rates of curvature which are constant and equal, wherein said first end further includes a remote edge and wherein each of said two opposed side edges terminate into said remote edge which has a rate of curvature which is less than the respective rates of curvature of said first and second opposed side edges, wherein said body further includes a second end having a second remote edge which has no curvature and third and fourth opposed side edges which have respective rates of curvature which are constant and equal and wherein each of said third and fourth opposed side edges terminate into said second remote edge and wherein said respective rates of curvature of said third and fourth opposed side edges are substantially less than said respective rates of curvature of said first and second opposed side edges and wherein said body further includes a narrow middle portion having a constant width, a first longitudinal axis of symmetry, and which terminates into said first and second end; and wherein said absorbent member further includes a generally rectangular adhesive strip which has a second longitudinal axis of symmetry which is orthogonal to said first longitudinal axis of symmetry, which is pliable, and which has a center portion which is coupled to said middle portion and which has two and substantially identical adhesive bearing ends which project away from said middle portion; and wherein said absorbent member further includes second and third adhesive strips which each include a respective first end which is respectively coupled to said first and second ends of said body and which each include a respective second adhesive bearing end which respectively project away from said first and second ends of said body and wherein each of said adhesive strips have a respective third and fourth longitudinal axis of symmetry and wherein each of said third and fourth longitudinal axes of symmetry overlay said first longitudinal axis of symmetry.

2. The absorbent member of claim 1 wherein said second and third adhesive strips are substantially identical.

3. The absorbent member of claim 2 wherein said first adhesive member is wider than said second and third adhesive member.

4. The absorbent member of claim 3 wherein first end of said body is generally goblet shaped.

5. The absorbent member of claim 4 wherein said second end of said body is generally elliptically shaped.

6. The absorbent member of claim 5 wherein said body is flat.

7. The absorbent member of claim 6 wherein said body is formed from cotton material.

* * * * *